United States Patent [19]

Baker et al.

[11] Patent Number: 5,665,732
[45] Date of Patent: Sep. 9, 1997

[54] INDAZOLE DERIVATIVES

[75] Inventors: Raymond Baker, Green Tye; Janusz Jozef Kulagowski, Bishops Stortford; Paul David Leeson, Cambridge; Adrian Leonard Smith, Bishops Stortford, all of United Kingdom

[73] Assignee: Merck, Sharp & Dohme Ltd., Hoddeson, England

[21] Appl. No.: 530,226
[22] PCT Filed: Mar. 14, 1994
[86] PCT No.: PCT/GB94/00503
§ 371 Date: Sep. 8, 1995
§ 102(e) Date: Sep. 8, 1995
[87] PCT Pub. No.: WO94/21626
PCT Pub. Date: Sep. 29, 1994

[30] Foreign Application Priority Data

Mar. 18, 1993 [GB] United Kingdom ............... 9305641

[51] Int. Cl.⁶ .................. A61K 31/435; A61K 31/415; C07D 401/06
[52] U.S. Cl. ............ 514/307; 514/322; 514/339; 514/403; 546/150; 546/199; 546/256; 548/207
[58] Field of Search ............ 514/322, 339, 514/403, 307; 546/199, 256, 150; 548/207

[56] References Cited

U.S. PATENT DOCUMENTS

| 3,488,353 | 1/1970 | Archer | 544/371 |
| 3,678,059 | 7/1972 | Gschwend et al. | 548/362.5 |
| 5,432,177 | 7/1995 | Baker et al. | 514/253 |

FOREIGN PATENT DOCUMENTS

| 0 449 186 A2 | 10/1991 | European Pat. Off. |
| 0 518 805 A1 | 12/1992 | European Pat. Off. |
| 518805 | 12/1992 | European Pat. Off. |
| 9400503 | 9/1994 | WIPO |

OTHER PUBLICATIONS

Kochetkov, N.K., Dudykina, N.V., "Substituted Indazole-3-Carboxamides and 3-Aminomethylindazoles" J.Gen.Chem. USSR, 32, pp. 189-191, 1962.

*Primary Examiner*—C. Warren Ivy
*Assistant Examiner*—Lyman H. Smith
*Attorney, Agent, or Firm*—Robert J. North; Melvin Winokur

[57] ABSTRACT

A class of chemical compounds comprising a 1-H-indazole moiety and a substituted heterocyclic moiety, linked via the 3-position of the indazole moiety by a methylene group, are ligands for dopamine receptor subtypes within the body and are therefore useful in the treatment and/or prevention of disorders of the dopamine system, in particular schizophrenia. In formula (I) R represents hydrogen or $C_{1-6}$ alkyl, Q represents a moiety of formula Qa, Qb, or Qc.

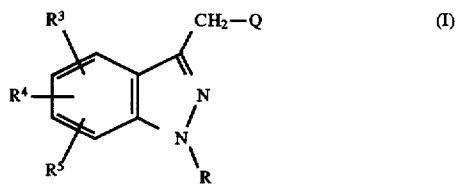

(I)

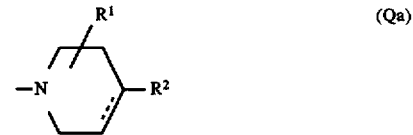

(Qa)

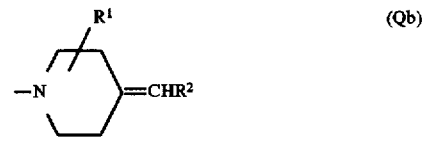

(Qb)

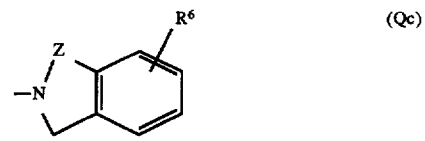

(Qc)

8 Claims, No Drawings

INDAZOLE DERIVATIVES

This application is a 35 U.S.C. 371 National Stage filing of PCT/BG94/000503 published as WC 94/21626 on Sep. 24, 1994.

This invention relates to a particular class of heteroaromatic compounds. More particularly, the invention is concerned with substituted indazole derivatives which are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The disclosure of U.S. Pat. No. 3,678,059 generically encompasses inter alia a class of 3-[piperidin-1-ylalkyl] indazole derivatives substituted on the indazole nitrogen atom by an araliphatic or aromatic radical. These compounds are alleged therein to possess antidepressant and anti-inflammatory activity. There is, however, no suggestion in U.S. Pat. No. 3,678,059 that such compounds would be of benefit in the treatment and/or prevention of disorders of the dopamine system.

The generic disclosure of EP-A-0449186 encompasses inter alia a series of substituted piperidin-1-ylalkyl-indazole derivatives which are stated to be antipsychotic agents that act by selective antagonism of the sigma receptor. There is, however, no specific disclosure therein of a [4-substituted-piperidin-1-ylmethyl]-1H-indazole derivative. Moreover, there is no suggestion in EP-A-0449186 that the compounds described therein would be of benefit in the treatment and/or prevention of disorders of the dopamine system. Indeed, it is explicitly stated in EP-A-0449186 that the compounds described therein do not bind to the dopamine receptors or only have weak binding for the dopamine receptors.

The compounds in accordance with the present invention, being ligands for dopamine receptor subtypes within the body, are accordingly of use in the treatment and/or prevention of disorders of the dopamine system.

The present invention accordingly provides a compound of formula I, or a salt or prodrug thereof:

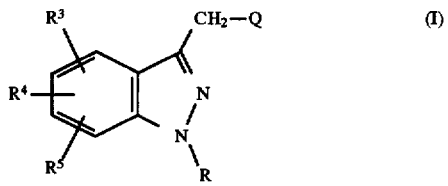

wherein

R represents hydrogen or $C_{1-6}$ alkyl;

Q represents a moiety of formula Qa, Qb or Qc:

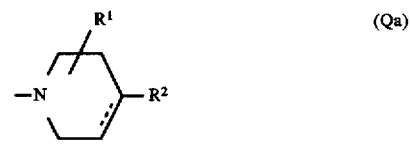

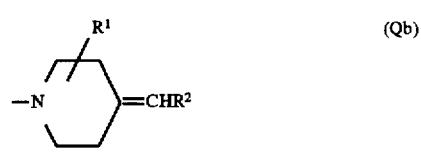

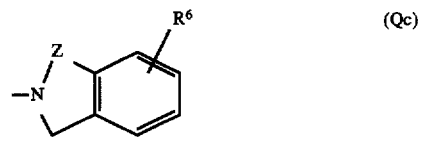

in which the broken line represents an optional chemical bond;

$R^1$ represents hydrogen, or an optionally substituted $C_{1-6}$ alkyl, $C_{1-6}$ alkoxy, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$) alkyl, aryl($C_{1-6}$)alkoxy, aryl($C_{2-6}$)alkenyl, aryl($C_{2-6}$) alkynyl, heteroaryl, heteroaryl($C_{1-6}$)alkyl, heteroaryl ($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{1-6}$) alkoxy, aryl($C_{2-6}$)alkenyl, aryl($C_{2-6}$)alkynyl, heteroaryl, heteroaryl($C_{1-6}$)alkyl, heteroaryl($C_{2-6}$) alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

Z represents —$CH_2$— or —$CH_2CH_2$—;

$R^6$ represents hydrogen, $C_{1-6}$ alkyl, $C_{1-6}$ alkoxy, aryl($C_{1-6}$)alkyl or halogen; and $R^a$ and $R^b$ independently represent hydrogen, hydrocarbon or a heterocyclic group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl ($C_{2-6}$)alkenyl and aryl ($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$, $R^2$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups within the scope of the term "hydrocarbon" and within the definition of the substituents $R^1$ and $R^2$ include groups containing from 3 to 7 carbon atoms. Particular cycloalkyl groups are cyclopropyl and cyclohexyl.

Particular cycloalkyl($C_{1-6}$)alkyl groups within the scope of the term "hydrocarbon" and within the definition of the substituents $R^1$ and $R^2$ include cyclopropylmethyl, cyclohexylmethyl and cyclohexylethyl.

Particular aryl groups within the scope of the term "hydrocarbon" and within the definition of the substituents $R^1$ and $R^2$ include phenyl and naphthyl.

Particular aryl($C_{1-6}$)alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

A particular aryl($C_{2-6}$)alkynyl group within the scope of the term "hydrocarbon" and within the definition of the substituents $R^1$ and $R^2$ is phenylethynyl.

Suitable heterocycloalkyl groups include azetidinyl, pyrrolidyl, piperidyl, piperazinyl and morpholinyl groups.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridylmethyl, pyrimidinylmethyl and pyrazinylmethyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R", —NR'COR", —NR"CO$_2$R", —NR'SO$_2$R", —CH$_2$NR'SO$_2$R", —NHCONR'R", —CONR'R", —SO$_2$NR'R" and —CH$_2$SO$_2$NR'R", in which R' and R" independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituent R represents hydrogen or methyl, especially hydrogen.

Suitably, the substituent $R^1$ represents hydrogen or methyl, especially hydrogen.

Suitable values for the substituent $R^2$ include $C_{1-6}$ alkyl, $C_{3-7}$ cycloalkyl($C_{1-6}$)alkyl, aryl, aryl($C_{1-6}$)alkyl, aryl($C_{2-6}$) alkenyl and heteroaryl, any of which groups may be optionally substituted. Examples of optional substituents on the group $R^2$ include $C_{1-6}$ alkyl, halogen, trifluoromethyl, $C_{1-6}$ alkoxy, $C_{1-3}$ alkylenedioxy, nitro and $C_{2-6}$ alkylcarbonyl.

Particular values of $R^2$ include methyl, ethyl, n-propyl, isopropyl, cyclohexyl-ethyl, phenyl, methylphenyl, ethylphenyl, fluorophenyl, chlorophenyl, trifluoromethyl-phenyl, methoxyphenyl, methylenedioxyphenyl, acetylphenyl, nitrophenyl, naphthyl, benzyl, chlorobenzyl, methylenedioxy-benzyl, phenethyl, phenylethenyl, benzofuryl, indolyl, pyridyl, chloropyridyl, methylpyridyl, methoxypyridyl, quinolyl, isoquinolyl and pyrimidinyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy.

Particular values of $R^6$ include hydrogen, chloro and bromo.

One sub-class of compounds according to the invention is represented by the compounds of formula IIA, and salts and prodrugs thereof:

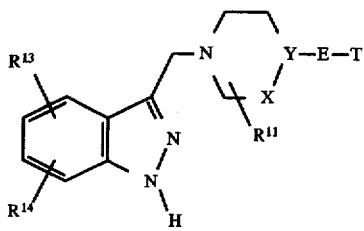
(IIA)

wherein

E represents —$(CH_2)_n$—, —CH=CH— or —C≡C—;
n is zero, 1, 2 or 3;

—X—Y— represents —$CH_2$—CH— or —CH=C—;

T represents a group of formula (i), (ii), (iii) or (iv):

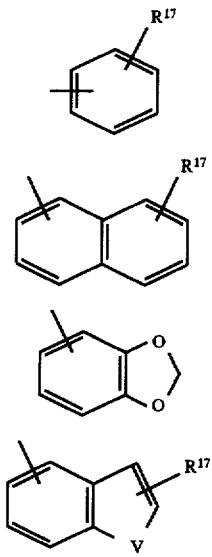

in which V represents oxygen, sulphur or NH;
$R^{11}$ represents hydrogen or $C_{1-6}$ alkyl; and
$R^{13}$, $R^{14}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Particular values of $R^{11}$ include hydrogen and methyl, especially hydrogen.

Particular values of $R^{13}$ and $R^{14}$ include hydrogen, halogen, methyl, ethyl, methoxy and benzyloxy, especially hydrogen, fluoro and chloro. Suitably, one of $R^{13}$ and/or $R^{14}$ is hydrogen.

Particular values of $R^{17}$ include hydrogen, fluoro, chloro, trifluoromethyl, methyl, methoxy, acetyl and nitro.

A particular subset of the compounds of formula IIA as defined above is represented by the compounds of formula IIB, and salts and prodrugs thereof:

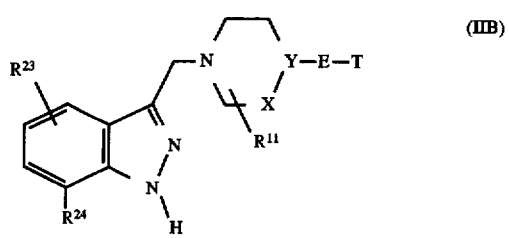
(IIB)

wherein

X, Y, $R^{11}$, E and T are as defined with reference to formula IIA above; and $R^{23}$ and $R^{24}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

Particular values of $R^{23}$ and $R^{24}$ include hydrogen, halogen, methyl, ethyl, methoxy and benzyloxy, especially hydrogen, fluoro and chloro. Suitably, $R^{24}$ is hydrogen, fluoro or chloro.

Another subset of the compounds of formula IIA as defined above is represented by the compounds of formula IIC, and salts and prodrugs thereof:

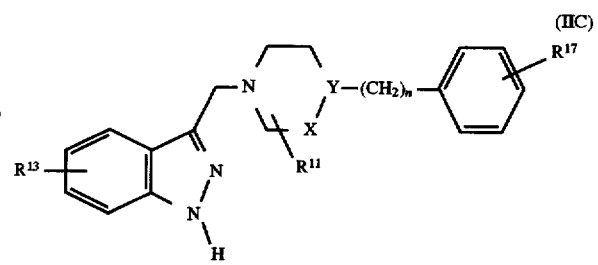
(IIC)

wherein n, X, Y, $R^{11}$, $R^{13}$ and $R^{17}$ are as defined with reference to formula IIA above.

A further sub-class of compounds according to the invention is represented by the compounds of formula IID, and salts and prodrugs thereof:

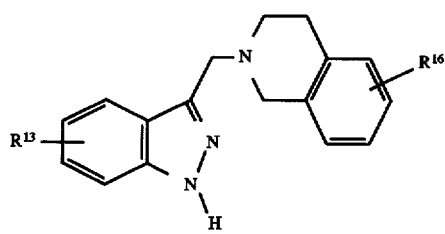
(IID)

wherein $R^{13}$ is as defined with reference to formula IIA above; and
$R^{16}$ represents hydrogen, $C_{1-6}$ alkyl, $C_{1-6}$ alkoxy, aryl($C_{1-6}$)alkyl or halogen.

Particular values of $R^{16}$ include hydrogen, chloro and bromo, especially hydrogen.

Specific compounds within the scope of the present invention include:

3-(1,2,3,4-tetrahydroisoquinolin-2-ylmethyl)-1H-indazole;
3-[4-(2-phenylethyl)piperidin-1-ylmethyl]-1H-indazole;
3-[4-(2-cyclohexylethyl)piperidin-1-ylmethyl]-1H-indazole;
6-fluoro-3-(1,2,3,4-tetrahydroisoquinolin-2-ylmethyl)-1H-indazole;
7-chloro-3-(1,2,3,4-tetrahydroisoquinolin-2-ylmethyl)-1H-indazole;

6-chloro-3-(1,2,3,4-tetrahydroisoquinolin-2-ylmethyl)-1H-indazole;

7-chloro-3-[4-(2-phenylethyl)-3,6-dihydro-2H-pyridin-1-ylmethyl]-1H-indazole;

(E)-3-[4-(2-phenylethenyl)-3,6-dihydro-2H-pyridin-1-ylmethyl]-1H-indazole;

7-chloro-(E)-3-[4-(2-phenylethenyl)-3,6-dihydro-2H-pyridin-1-ylmethyl]-1H-indazole;

3-[4-(naphthalen-2-yl)-3,6-dihydro-2H-pyridin-1-ylmethyl]-1H-indazole;

7-chloro-3-[4-(4-chlorophenyl)-3,6-dihydro-2H-pyridin-1-ylmethyl]-1H-indazole;

3-[4-(4-methoxyphenyl)-3,6-dihydro-2H-pyridin-1-ylmethyl]-1H-indazole;

7-chloro-3-[4-(4-methoxyphenyl)-3,6-dihydro-2H-pyridin-1-ylmethyl]-1H-indazole;

7-fluoro-3-[4-(4-methoxyphenyl)-3,6-dihydro-2H-pyridin-1-ylmethyl]-1H-indazole;

6,7-difluoro-3-[4-(4-methoxyphenyl)-3,6-dihydro-2H-pyridin-1-ylmethyl]-1H-indazole;

3-[4-(benzofuran-5-yl)-3,6-dihydro-2H-pyridin-1-ylmethyl]-1H-indazole;

3-[4-(benzofuran-5-yl)-3,6-dihydro-2H-pyridin-1-ylmethyl]-7-chloro-1H-indazole;

3-[4-(benzo[1,3]dioxolan-5-yl)-3,6-dihydro-2H-pyridin-1-ylmethyl]-1H-indazole;

3-[4-(1H-indol-5-yl)-3,6-dihydro-2H-pyridin-1-ylmethyl]-1H-indazole;

7-chloro-3-[4-(1H-indol-5-yl)-3,6-dihydro-2H-pyridin-1-ylmethyl]-1H-indazole;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

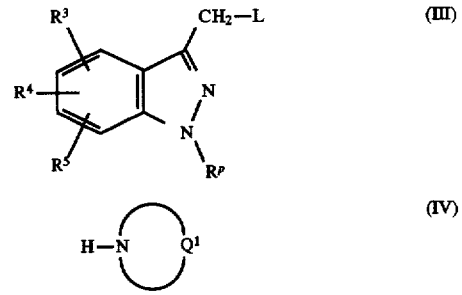

wherein $R^3$, $R^4$ and $R^5$ are as defined above, $Q^1$ represents the residue of a moiety of formula Qa to Qc as defined above, L represents a suitable leaving group, and $R^p$ corresponds to the group R as defined above or represents a suitable protecting group; followed, where required, by removal of the protecting group $R^p$; and subsequently, if necessary, N-alkylation by standard methods to introduce the moiety R.

The leaving group L is suitably a halogen atom, e.g. bromine.

The protecting group $R^p$ on the indazole nitrogen atom, when present, is suitably an acyl moiety such as acetyl, which can conveniently be removed as necessary by treatment under strongly basic conditions, e.g. sodium methoxide in methanol. Alternatively, the protecting group $R^p$ may be a carbamoyl moiety such as t-butoxycarbonyl (BOC), which can conveniently be removed as necessary by treatment under mildly acidic conditions.

The reaction between compounds III and IV is conveniently carried out by stirring the reactants under basic conditions in a suitable solvent, for example potassium carbonate in N,N-dimethylformamide; triethylamine in tetrahydrofuran or acetonitrile; or diisopropylethylamine (Hünig's base) in dichloromethane.

In an alternative procedure, the compounds in accordance with the present invention may be prepared by a process which comprises reducing a compound of formula V:

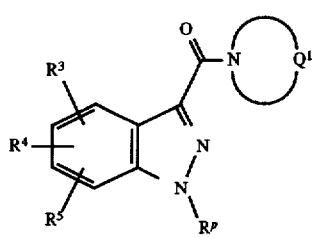

(V)

wherein $Q^1$, $R^3$, $R^4$, $R^5$ and $R^P$ are as defined above; followed, where required, by removal of the protecting group $R^P$; and subsequently, if necessary, N-alkylation by standard methods to introduce the moiety R.

The reaction is conveniently carried out by treating the compound V with a reducing agent such as lithium aluminium hydride in an appropriate solvent, e.g. tetrahydrofuran.

The intermediates of formula V above may suitably be prepared by reacting a compound of formula IV as defined above with a compound of formula VI:

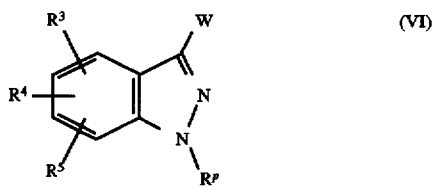

(VI)

wherein $R^3$, $R^4$, $R^5$ and $R^P$ are as defined above; and W represents a reactive carboxylate moiety.

Suitable values for the reactive carboxylate moiety W include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula VI above wherein W is an acid chloride moiety may be prepared by treating the corresponding carboxylic acid derivative with thionyl chloride in toluene. Similarly, the intermediates of formula VI wherein W is an acylimidazole moiety may be prepared by treating the corresponding carboxylic acid derivative with 1,1'-carbonyldiimidazole. Alternatively, the reactive carboxylate moiety W may be obtained by treating the corresponding compound wherein W is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula IV.

Where they are not commercially available, the starting materials of formula III, IV and VI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mMTris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLES

General techniques: All reactions were carried out under a nitrogen atmosphere using anhydrous solvents under anhydrous conditions unless otherwise noted. Yields refer to chromatographically (HPLC/TLC) and spectroscopically ($^1$H NMR) homogeneous materials, unless otherwise stated.

All reactions were monitored by thin-layer chromatography carried out on 0.25 mm E. Merck silica gel plates (60F-254) using UV light and/or $I_2$ vapour for visualisation. Fluka silica gel (60, particle size 0.035–0.070 mm) was used for flash chromatography.

EXAMPLE 1

2-(1H-Indazol-3-ylmethyl)-1,2,3,4-tetrahydroisoquinoline

1H-Indazole-3-carboxylic acid (1.50 g, 9.25 mmol), 1,2,3,4-tetrahydroisoquinoline (1.60 g, 12 mmol), 1-hydroxybenzotriazole hydrate (1.65 g, 12 mmol) and 1-(3-dimethylaminopropyl)-3-ethyl-carbodiimide hydrochloride (2.35 g, 12 mmol) were dissolved in dichloromethane ($CH_2Cl_2$, 50 mL) and the solution was stirred at 20° C. for 14 h. The solution was poured into 2M aqueous HCl (100 mL) and extracted with $CH_2Cl_2$ (3×100 mL). The combined organic extracts were washed with saturated aqueous $NaHCO_3$ (50 mL), dried ($MgSO_4$) and concentrated to give a yellow solid (2.67 g) which was sparingly soluble in $CH_2Cl_2$ or ethyl acetate (EtOAc); mp 199°–200° C. (from EtOAc).

A solution of the above solid (2.67 g, 9.25 mmol) in tetrahydrofuran (THF, 25 mL) was treated with $LiAlH_4$ (24 mL of a 1.0M solution in THF, 24 mmol) and the resulting solution was heated at 60° C. for 14 h. The solution was cooled, quenched by the cautious addition of 2M aqueous NaOH (4 mL), stirred for 1 h at 20° C., filtered washing with EtOAc, and the filtrate was concentrated and the residue purified by flash chromatography (50% EtOAc in hexane) to give the free base of the title compound as a colourless viscous oil.

The oil was dissolved in methanol (20 mL) and added to a solution of oxalic acid (1.0 g, 11 mmol) in methanol (10 mL). The solution was diluted with $Et_2O$ (400 mL) and the oxalate salt (2.10 g, 62% based upon 1H-indazole-3-carboxylic acid) precipitated as a fine white crystalline powder which was collected by filtration, washing with $Et_2O$; mp 151°–152° C. (from MeOH/$Et_2O$); $^1H$ NMR (360 MHz, $d_6$-DMSO) d 7.91 (d, J=8.0 Hz, 1H, aromatic), 7.54 (d, J=8.4 Hz, 1H, aromatic), 7.37 (dt, J=0.8, 6.7 Hz, 1H, aromatic), 7.17–7.06 (m, 5H, aromatic), 5.0–4.0 (bs, 4H, NH, $(COOH)_2$, $H_2O$), 4.36 (s, 2H, $CH_2$—N), 3.99 (s, 2H, indazole-$CH_2$—N), 3.11 (bs, 2H, $CH_2CH_2$—N), 2.93 (t, J=5.9 Hz, $CH_2CH_2$—N); MS (CI+) m/e 264 (M+H$^+$); Anal. calcd for $C_{17}H_{17}N_3.(COOH)_2.H_2O$: C, 62.97; H, 5.56; N, 11.60. Found: C, 63.00; H, 5.48; N, 11.60.

EXAMPLE 2

3-(4-Phenethylpiperidin-1-ylmethyl)-1H-indazole

Step A: 1-Acetyl-3-methyl-1H-indazole

3-Methyl-1H-indazole (6.157 g, 44.6 mmol) in $CH_2Cl_2$ (100 mL) was treated with acetic anhydride (22.75 g, 223 mmol), triethylamine (22.5 g, 228 mmol) and DMAP (0.54 g, 4.5 mmol). The mixture was stirred 1 h at 20° C., poured into water (100 mL) and extracted with $CH_2Cl_2$ (2×100 mL). The extracts were dried ($Na_2SO_4$), concentrated and the residue recrystallised from hexane to give the title compound (4.12 g, 66%) as a white crystalline solid; mp 70°–71° C. (from hexane); $^1H$ NMR (360 MHz, $CDCl_3$) δ 8.41 (d, J=8.4 Hz, 1H, indazole), 7.64 (d, J=8.4 Hz, 1H, indazole), 7.54 (t, J=8.4 Hz, 1H, indazole), 7.35 (t, J=8.4 Hz, 1H, indazole), 2.75 (s, 3H, Ac), 2.58 (s, 3H, Me); MS (CI+) m/e 175 (M+H$^+$); Anal. calcd for $C_{10}H_{10}N_2O$: C, 68.95; H, 5.97; N, 16.08. Found: C, 68.80; H, 5.58; N, 16.18.

Step B: 1-Acetyl-3-bromomethyl-1H-indazole

1-Acetyl-3-methyl-1H-indazole (5.77 g, 33.1 mmol) in $CCl_4$ (150 mL) was treated with N-bromosuccinimide (6.49 g, 36.5 mmol) and benzoyl peroxide (0.80 g, 3.3 mmol) and the mixture was heated at 70° C. for 16 h. The mixture was concentrated and the residue quickly filtered through a plug of flash silica eluting with 0→5% EtOAc in hexane to give the crude title compound contaminated with traces of dibromide and starting material. This was conveniently used directly in subsequent reactions without further purification.

Step C: 3-(-4-Phenethylpiperidin-1-ylmethyl)-1H-indazole

1-Acetyl-3-bromomethyl-1H-indazole (0.50 g, 1.98 mmol) in $CH_2Cl_2$ (25 mL) was treated with 4-phenethylpiperidine hydrochloride (0.893 g, 3.96 mmol) and Hünig's base (0.78 g, 5.94 mmol) and the mixture stirred at 20° C. for 16 h. The mixture was poured into saturated aqueous sodium bicarbonate solution (25 mL) and extracted with $CH_2Cl_2$ (3×25 mL). The combined organic extracts were dried ($MgSO_4$), concentrated and the residue purified by flash chromatography (0%→10% EtOAc in hexane) to give 1-acetyl-3-(4-phenethylpiperidin-1-ylmethyl)-1H-indazole as a colourless oil (98 mg, 14%). This was dissolved in $CH_2Cl_2$/methanol (1:1, 10 mL), treated with NaOMe (2 mg) and stirred for 15 min at 20° C. The mixture was poured into saturated aqueous sodium bicarbonate solution (25 mL) and extracted with $CH_2Cl_2$ (3×25 mL). The combined organic extracts were dried ($MgSO_4$), concentrated and the residue recrystallised from EtOAc/hexane to give the title compound (55 mg, 69%) as colourless crystals; mp 153°–155° C. (from EtOAc/hexane); $^1H$ NMR (360 MHz, $d_6$-DMSO) δ 12.75 (bs, 1H, NH), 7.84 (d, J=8.1 Hz, 1H, indazole), 7.46 (d, J=8.4 Hz, 1H, indazole), 7.31 (t, J=6.7 Hz, 1H, indazole), 7.27–7.12 (m, 5H, Ph), 7.07 (t, J=7.1 Hz, 1H, indazole), 3.78 (s, 2 H, Ar—$CH_2N$), 2.85 (m, 2 H, aliphatic), 2.56 (m, 2 H, aliphatic), 1.94 (m, 2H, aliphatic), 1.65 (m, 2H, aliphatic), 1.47 (m, 2H, aliphatic), 1.16 (m, 3H, aliphatic); MS (CI+) m/e 320 (M+H$^+$); Anal. calcd for $C_{21}H_{25}N_3$: C, 78.96; H, 7.89; N, 13.15. Found: C, 78.94; H, 7.96; N, 12.89.

EXAMPLE 3

3-[4-(2-Cyclohexylethyl)piperidin-1-ylmethyl]-1H-indazole

The title compound was prepared as a white crystalline solid following the general procedure described in EXAMPLE 2; mp 145° 146° C. (from EtOAc); $^1H$ NMR (360 MHz, $d_6$-DMSO) δ 12.75 (bs, 1H, NH), 7.83 (d, J=8.1 Hz, 1H, indazole), 7.46 (d, J=8.4 Hz, 1H, indazole), 7.31 (t, J=6.7 Hz, 1H, indazole), 7.07 (t, J=7.1 Hz, 1H, indazole), 3.78 (s, 2H, Ar—$CH_2N$), 2.83 (m, 2H, aliphatic), 1.93 (m, 2H, aliphatic), 1.63 (m, 7H, aliphatic), 1.14 (m, 11H, aliphatic), 0.85 (m, 2H, aliphatic); MS (CI+) m/e 326 (M+H$^+$); Anal. calcd for $C_{21}H_{31}n_3$: C, 77.49; H, 9.60; N, 12.91. Found: C, 77.38; H, 9.59; N, 12.72.

EXAMPLE 4

2-(6-Fluoro-1H-indazol-3-ylmethyl)-1,2,3,4-tetrahydroisoquinoline

Step A: 1-(2-Amino-4-fluorophenyl)ethanone

A solution of $BCl_3$ (110 mL of a 1.0M solution in $CH_2Cl_2$, 110 mmol) was cooled to 0° C. and treated with a solution of 3-fluoroaniline (10 mL, 104 mmol) in 1,1,2,2-tetrachloroethane (200 mL). The resulting solution was stirred 15 min and treated with MeCN (16.3 mL, 330 mmol) and $AlCl_3$ (14.7 g, 110 mmol) and heated at 120° C. for 16 h with distillative removal of $CH_2Cl_2$. The mixture was cooled to 0° C. and quenched with 2M aqueous HCl (250 mL). The mixture was heated at 80° C. for 1 h to hydrolyse the imine, and extracted with $CH_2Cl_2$ (5×100 mL). The combined organic extracts were dried ($MgSO_4$), concentrated and purified by flash chromatography (10% EtOAc in hexane) to give the title compound (9.618 g, 60%) as a low melting pale yellow crystalline solid; $^1H$ NMR (360 MHz, $d_6$-DMSO) δ 7.81 (dd, J=8.9, 6.7 Hz, 1H, Ph), 7.43 (bs, 2H, $NH_2$), 6.49 (dd, J=12.0, 2.6 Hz, 1H, Ph), 6.35 (dt, J=8.9, 0.7 Hz, 1H, Ph), 2.48 (s, 3H, Me).

Step B: 6-Fluoro-3-methyl-1H-indazole 1-(2-Amino-4-fluorophenyl)ethanone (9.618 g, 62.9 mmol) was treated with concentrated hydrochloric acid (16 mL) and water (16 mL), and the resulting white suspension was cooled to −10° C. and treated with a solution of sodium nitrite (4.338 g, 62.9 mmol) in 10 mL $H_2O$, maintaining the temperature below 0° C. The resulting solution was filtered directly into a rapidly stirred solution of $SnCl_2.2H_2O$ (34 g in 200 mL $H_2O$) and the resulting mixture was stirred for 1 h at 20° C., basified (32 g NaOH in 200 mL $H_2O$) and extracted with EtOAc. The combined organic extracts were dried ($MgSO_4$), concentrated and the residue purified by flash chromatography (25% EtOAc in hexane) to give the title compound (3.10 g, 33%) as a white solid; mp 116°–117° C. (from hexane); $^1$H NMR (360 MHz, $CDCl_3$) δ12.89 (bs, 1H, NH), 7.62 (dd, J=8.8, 5.1 Hz, 1H, indazole), 7.09 (dd, J=9.1, 2.0 Hz, 1H, indazole), 6.93 (dt, J=9.1, 2.0 Hz, 1H, indazole), 2.60 (s, 3H, Me); MS (CI+) m/e 151 (M+H$^+$); Anal. calcd for $C_8H_7FN_2$: C, 63.99, H, 4.70; N, 18.66. Found: C, 63.94; H, 4.72; N, 19.10.

Step C: 1-Acetyl-6-fluoro-3-methyl-1H-indazole

6-Fluoro-3-methyl-1H-indazole (2.79 g, 18.6 mmol) in $CH_2Cl_2$ (50 mL) was treated with acetic anhydride (2.8 g, 30 mmol), Hünig's base (5.2 mL, 30 mmol) and DMAP (0.2 g, 1.7 mmol). The mixture was stirred 1 h at 20° C., poured into water (100 mL) and extracted with $CH_2Cl_2$ (2×100 mL). The extracts were dried ($Na_2SO_4$), concentrated and the residue recrystallised from hexane to give the title compound (3.41 g, 96%) as a white crystalline solid; mp 89°–91° C. (from hexane); $^1$H NMR (360 MHz, $CDCl_3$) δ 8.05 (dd, J=9.4, 2.2 Hz, 1H, indazole), 7.51 (dd, J=8.7, 5.1 Hz, 1H, indazole), 7.03 (dt, J=8.8, 2.2 Hz, 1H, indazole), 2.67 (s, 3H, Me), 2.49 (s, 3H, Ac); MS (CI+) m/e 193 (M+H$^+$); Anal. calcd for $C_{10}H_9FN_2O$: C, 62.49; H, 4.72; N, 14.58. Found: C, 62.50; H, 4.79; N, 14.63.

Step D: 1-Acetyl-3-bromomethyl-6-fluoro-1H-indazole

1-Acetyl-6-fluoro-3-methyl-1H-indazole (5.77 g, 33.1 mmol) in $CCl_4$ (100 mL) was treated with NBS (3.64 g, 20 mmol) and benzoyl peroxide (0.388 g, 1.6 mmol) and the mixture was heated at 70° C. for 6 h. The mixture was concentrated and the residue quickly filtered through a plug of flash silica eluting with 2%→7% EtOAc in hexane to give the crude title compound (2.97 g, 65%) contaminated with traces of dibromide and starting material. This was conveniently used directly in subsequent reactions without further purification.

1-Acetyl-3-bromomethyl-6-chloro-1H-indazole, 1-acetyl-3-bromomethyl-7-iodo-1H-indazole, 1-acetyl-3-bromomethyl-7-fluoro-1H-indazole, 1-acetyl-3-bromomethyl-6,7-difluoro-1H-indazole, and 1-acetyl-3-bromomethyl-7-chloro-1H-indazole were similarly prepared from 3-chloroaniline, 2-iodoaniline, 2-fluoroaniline, 2,3-difluoroaniline and 2-chloroaniline, respectively.

Step E: 2-(1-Acetyl-6-fluoro-1H-indazol-3-ylmethyl)-1,2,3,4-tetrahydroisoquinoline 1-Acetyl-3-bromomethyl-6-fluoro-1H-indazole (0.53 g, 1.96 mmol) in $CH_2Cl_2$ (10 mL) was treated with 1,2,3,4-tetrahydroisoquinoline (0.261 g, 1.96 mmol) and Hünig's base (0.44 mL, 2.5 mmol) and the mixture stirred at 20° C. for 16 h. The mixture was poured into saturated aqueous sodium bicarbonate solution (25 mL) and extracted with $CH_2Cl_2$ (3×25 mL). The combined organic extracts were dried ($MgSO_4$), concentrated and the residue purified by flash chromatography (7%→12% EtOAc in hexane) to give the title compound as a white solid (475 mg, 53%); mp 106°–107° C. (from $Et_2O$/hexane); $^1$H NMR (360 MHz, $d_6$-DMSO) δ 8.08 (dd, J=8.8, 5.4 Hz, 1H, indazole), 8.00 (dd, J=9.6, 2.2 Hz, 1H, indazole), 7.29 (dt, J=9.1, 2.5 Hz, 1H, indazole), 7.10 (m, 3H, tetrahydroisoquinoline), 7.02 (m, 1H, tetrahydroisoquinoline), 4.05 (s, 2H, Ar—$CH_2$N), 3.68 (s, 2H, Ar—$CH_2$N)), 2.79 (m, 4H, tetrahydroisoquinoline)2.72 (s, 3H, Ac); MS (CI+) m/e 324 (M+H$^+$); Anal. calcd for $C_{19}H_{18}FN_3O$: C, 70.57; H, 5.61; N, 12.99. Found: C, 70.28; H, 5.32; N, 12.84.

Step F: 2-(6-Fluoro-1H-indazol-3-ylmethyl)-1,2,3,4-tetrahydroisoquinoline 2-(1-Acetyl-6-fluoro-1H-indazol-3-ylmethyl)-1,2,3,4-tetrahydroisoquinoline (300 mg, 0.93 mmol) in $CH_2Cl_2$/MeOH (1:1, 10 mL) was treated with sodium methoxide (2 mg) and stirred for 15 min at 20° C. The mixture was poured into saturated aqueous sodium bicarbonate solution (25 mL) and extracted with $CH_2Cl_2$ (3×50 mL). The combined organic extracts were dried ($MgSO_4$), concentrated and purified by flash chromatography (50% EtOAc in hexane) to give the title compound as a colourless oil. Conversion to the hydrogen oxalate salt in MeOH/$Et_2O$ gave colourless crystals (202 mg, 59%); mp 200°–201° C. (from MeOH/$Et_2O$); $^1$H NMR (360 MHz, $d_6$-DMSO) d 7.93 (dd, J=8.8, 5.3 Hz, 1H, indazole), 7.30 (dd, J=9.7, 2.8 Hz, 1H, indazole), 7.15–6.97 (m, 5H, aromatic), 4.25 (s, 2H, Ar—$CH_2$N), 3.88 (s, 2H, Ar—$CH_2$N), 3.00 (bs, 2H, tetrahydroisoquinoline), 2.89 (bs, 2H, tetrahydroisoquinoline); MS (CI+) m/e 282 (M+H$^+$); Anal. calcd for $C_{17}H_{16}FN_3 \cdot (COOH)_2 \cdot H_2O$: C, 65.35; H, 5.33; N, 12.71. Found: C, 65.40; H, 5.24; N, 12.49.

EXAMPLE 5

2-(6-Chloro-1H-indazol-3-ylmethyl)-1,2,3,4-tetrahydroisoquinoline

The hydrogen oxalate salt of the title compound was prepared as a white crystalline solid following the general procedure described in EXAMPLE 4; mp 212°–214° C. (from EtOAc); $^1$H NMR (360 MHz, $d_6$-DMSO) δ 13.3 (bs, 1H, NH), 7.94 (d, J=8.7 Hz, 1H, indazole), 7.63 (s, 1H, indazole), 7.18–7.09 (m, 5H, aromatic), 4.36 (s, 2H, Ar—$CH_2$N), 3.98 (s, 2H, Ar—$CH_2$N), 3.10 (bs, 2H, $CH_2$N), 2.92 (bs, 2H, $CH_2$—Ar); MS (CI+) m/e 298 (M+H$^+$); Anal. calcd for $C_{17}H_{16}N_3ClOC_2O_4H_2o \ H_2O$: C, 57.51; H, 4.83; N, 10.58. Found: C, 57.74; H, 4.66; N, 10.32.

EXAMPLE 6

2-(7-Chloro-1H-indazol-3-ylmethyl)-1,2,3,4-tetrahydroisoquinoline

The hydrogen oxalate salt of the title compound was prepared as a white crystalline solid following the general procedure described in EXAMPLE 4; mp 122°–124° C. (from EtOAc); $^1$H NMR (360 MHz, $d_6$-DMSO) δ 7.92 (d, J=7.9 Hz, 1H, indazole), 7.49 (d, J=6.9 Hz, 1H, indazole), 7.20–7.08 (m, 5H, aromatic), 4.44 (s, 2H, Ar—$CH_2$N), 4.05 (s, 2H, Ar—$CH_2$N), 3.17 (m, 2H, $CH_2$—N), 2.95 (m, 2H, $CH_2$—Ar); MS (CI+) m/e 297 (M+H$^+$); Anal. calcd for $C_{17}H_{16}N_3Cl \cdot C_2O_4H_2$. EtOAc: C, 57.80; H, 5.20; N, 9.63. Found: C, 57.41; H, 5.34; N, 9.83.

EXAMPLE 7

7-Chloro-3-(4-phenethyl-3,6-dihydro-2H-pyridin-1-ylmethyl)-1H-indazole

The title compound was prepared as a white crystalline solid following the general procedure described in EXAMPLE 4; mp 171°–172° C. (from EtOAc); $^1$H NMR (360 MHz, $d_6$-DMSO) δ 13.31 (bs, 1H, NH), 7.81 (d, J=7.9

Hz, 1H, indazole), 7.42 (d, J= 7.4 Hz, 1H, indazole), 7.27–7.07 (m, 6H, aromatic), 5.35 (s, 1H, olefinic), 3.88 (s, 2H, Ar—$CH_2$N), 2.91 (s, 2H, C=C—$CH_2$—N), 2.66 (t, J=7.7 Hz, 2H, $CH_2$), 2.55 (t, J=5.6 Hz, 2H, $CH_2$—C—N), 2.20 (t, J=7.7 Hz, 2H, $CH_2$), 2.04 (bs, 2H, $CH_2$—N); MS (CI+) m/e 352 (M+H$^+$); Anal. calcd for $C_{21}H_{22}N_3Cl$: C, 71.68; H, 6.30; N, 11.94. Found: C, 71.62; H, 6.07; N, 11.64.

EXAMPLE 8

3-(4-(E)-Styryl-3,6-dihydro-2H-pyridin-1-ylmethyl)-1H-indazole

The title compound was prepared as a white crystalline solid following the general procedure described in EXAMPLE 2; mp 207°–209° C. (from EtOAc); $^1$H NMR (360 MHz, $d_6$-DMSO) δ 12.83 (bs, 1H, NH), 7.86 (d, J=8.0 Hz, 1H, indazole), 7.51–7.45 (m, 2H, aromatic), 7.36–7.30 (m, 2H, aromatic), 7.23 (m, 1H, aromatic), 7.09 (m, 1H, aromatic), 6.89 (d, J=16.3 Hz, 1H, CH=C), 6.47 (d, J=16.3 Hz, 1H, C=CH), 5.90 (bs, 1H, olefinic), 3.94 (s, 2H, Ar—$CH_2$N), 3.14 (bs, 2H, C=C—$CH_2$—N), 2.67 (m, 2H, $CH_2$—C—N), 2.32 (bs, 2H, $CH_2$—N); MS (CI+) m/e 316 (M+H$^+$); Anal. calcd for $C_{21}H_{21}N_3O$ $H_2O$: C, 76.16; H, 6.92; N, 12.69. Found: C, 76.26; H, 6.42; N, 12.40.

EXAMPLE 9

7-Chloro-3-(4-(E)-styryl-3,6-dihydro-2H-pyridin-1-ylmethyl)-1H-indazole

The title compound was prepared as a white crystalline solid following the general procedure described in EXAMPLE 4; mp 223°–224° C. (from EtOAc); $^1$H NMR (360 MHz, $d_6$-DMSO) δ 13.12 (bs, 1H, NH), 7.82 (d, J=7.8 Hz, 1H, indazole), 7.43–7.37 (m, 3H, aromatic), 7.29 (m, 2H, aromatic), 7.18 (m, 1H, aromatic), 7.08 (m, 1H, aromatic), 6.82 (d, J=16.4 Hz, 1H, CH=C), 6.46 (d, J=16.4 Hz, 1H, C=CH), 5.87 (bs, 1H, olefinic), 3.96 (s, 2H, Ar—$CH_2$N), 3.16 (bs, 2H, C=C—$CH_2$—N), 2.69 (m, 2H, $CH_2$—C—N), 2.32 (bs, 2H, $CH_2$—N); MS (CI+) m/e 350 (M+H$^+$); Anal. calcd for $C_{21}H_{20}N_3Cl$: C, 72.09; H, 5.76; N, 12.01. Found: C, 72.14; H, 5.85; N, 11.99.

EXAMPLE 10

3-(4-Naphthalen-2-yl-3,6-dihydro-2H-pyridin-1-ylmethyl)-1H-indazole

The title compound was prepared as a white crystalline solid following the general procedure described in EXAMPLE 2; mp 225°–227° C. (from EtOAc); $^1$H NMR (360 MHz, $d_6$-DMSO) δ 12.83 (bs, 1H, NH), 7.90–7.83 (m, 5H, aromatic), 7.67 (m, 1H, aromatic), 7.51–7.43 (m, 3H, aromatic), 7.33 (t, J=7.1 Hz, 1H, indazole), 7.09 (t, J=7.6 Hz, 1H, indazole), 6.35 (bs, 1H, olefinic), 3.98 (s, 2H, Ar—$CH_2$N), 3.21 (m, 2H, C=C—$CH_2$—N), 2.77 (m, 2H, $CH_2$—C—N), 2.60 (bs, 2H, $CH_2$—N); MS (CI+) m/e 340 (M+H$^+$); Anal. calcd for $C_{23}H_{21}N_3O$ $H_2O$: C, 79.28; H, 6.36; N, 12.06. Found: C, 79.65; H, 6.22; N, 11.80.

EXAMPLE 11

7-Chloro-3-[4-(4-chlorophenyl)-3,6-dihydro-2H-pyridin-1-ylmethyl]-1H-indazole The title compound was prepared as a white crystalline solid following the general procedure described in EXAMPLE 4; mp 171°–173° C. (from EtOAc); $^1$H NMR (360 MHz, $d_6$-DMSO) δ 13.37 (bs, 1H, NH), 7.85 (d, J=8.0 Hz, 1H, indazole), 7.43 (d, J= 8.6 Hz, 3H, 2×Ph, 1×indazole), 7.36 (d, J=8.6 Hz, 2H, Ph), 7.10 (t, J=7.7 Hz, 1H, indazole), 6.19 (bs, 1H, olefinic), 3.96 (s, 2H, Ar—$CH_2$N), 3.15 (m, 2H, C=C—$CH_2$—N), 2.70 (t, J=5.6 Hz, 2H, $CH_2$—C—N), 2.44 (bs, 2H, $CH_2$—N); MS (CI+) m/e 358 (M+H$^+$); Anal. calcd for $C_{19}H_{17}N_3Cl_2O$ $H_2O$: C, 62.91; H, 4.86; N, 11.58. Found: C, 63.22; H, 4.66; N, 11.48.

EXAMPLE 12

3-[4-(4-Methoxyphenyl)-3,6-dihydro-2H-pyridin-1-ylmethyl]-1H-indazole

The title compound was prepared as a white crystalline solid following the general procedure described in EXAMPLE 2; mp 157°–159° C. (from EtOAc); $^1$H NMR (360 MHz, $d_6$-DMSO) δ 12.81 (bs, 1H, NH), 7.85 (d, J=8.1 Hz, 1H, indazole), 7.48 (d, J=8.4 Hz, 1H, indazole), 7.48 (d, J=8.4 Hz, 2H, Ph), 7.47 (t, J=8.4 Hz, 1H, indazole), 7.08 (t, J=7.8 Hz, 1H, indazole), 6.87 (d, J=8.9 Hz, 2H, Ph), 6.02 (bs, 1H, olefinic), 3.93 (s, 2H, Ar—$CH_2$N), 3.73 (s, 3H, OMe), 3.13 (m, 2H, C=C—$CH_2$—N), 2.69 (m, 2H, $CH_2$—C—N), 2.42 (bs, 2H, $CH_2$—N); MS (CI+) m/e 320 (M+H$^+$); Anal. calcd for $C_{20}H_{21}N_3O_o$ $H_2O$: C, 73.15; H, 6.75; N, 12.80. Found: C, 73.58; H, 6.45; N, 12.61.

EXAMPLE 13

7-Chloro-3-[4-(4-methoxyphenyl)-3,6-dihydro-2H-pyridin-1-ylmethyl]-1H-indazole The title compound was prepared as a white crystalline solid following the general procedure described in EXAMPLE 4; mp 201°–203° C. (from EtOAc); $^1$H NMR (360 MHz, $d_6$-DMSO) δ 13.36 (bs, 1H, NH), 7.85 (d, J=8.0 Hz, 1H, indazole), 7.43 (d, J= 7.4 Hz, 1H, indazole), 7.33 (d, J=8.8 Hz, 2H, Ph), 7.10 (t, J=7.8 Hz, 1H, indazole), 6.87 (d, J=8.8 Hz, 2H, Ph), 6.02 (bs, 1H, olefinic), 3.95 (s, 2H, Ar—$CH_2$N), 3.74 (s, 3H, OMe), 3.12 (m, 2H, C=C—$CH_2$N), 2.69 (t, J=5.6 Hz, 2H, $CH_2$—C—N), 2.42 (bs, 2H, $CH_2$—N); MS (CI+) m/e 354 (M+H$^+$); Anal. calcd for $C_{20}H_{20}N_3ClO$: C, 67.89; H, 5.70; N, 11.88. Found: C, 68.02; H, 5.59; N, 11.61.

EXAMPLE 14

7-Fluoro-3-[4-(4-methoxyphenyl)-3,6-dihydro-2H-pyridin-1-ylmethyl]-1H-indazole The title compound was prepared as a white crystalline solid following the general procedure described in EXAMPLE 4; mp 183°–185° C. (from EtOAc); $^1$H NMR (360 MHz, $d_6$-DMSO) δ 13.39 (bs, 1H, NH), 7.69 (d, J=8.0 Hz, 1H, indazole), 7.34 (d, J=8.7 Hz, 2H, Ph), 7.18 (m, 1H, indazole), 7.06 (m, 1H, indazole), 6.87 (d, J=8.7 Hz, 2H, Ph), 6.02 (bs, 1H, olefinic), 3.95 (Ar—$CH_2$—N), 3.73 (s, 3H, OMe), 3.12 (bs, 2H, C=C—$CH_2$—N), 2.69 (t, J=5.4 Hz, 2H, $CH_2$—C—N), 2.42 (bs, 2H, $CH_2$—N); MS (CI+) m/e 338 (M+H$^+$); Anal. calcd for $C_{20}H_{20}FN_3O_o$ $H_2O$: C, 70.26; H, 6.04; N, 12.29. Found: C, 70.35; H, 5.54; N, 12.37.

EXAMPLE 15

6,7-Difluoro-3-[4-(4-methoxyphenyl)-3,6-dihydro-2H-pyridin-1-ylmethyl]-1H-indazole The title compound was prepared as a white crystalline solid following the general procedure described in EXAMPLE 4; mp 195°–197° C. (from EtOAc); $^1$H NMR (360 MHz, $d_6$-DMSO) δ 13.54 (bs, 1H, NH), 7.70 (dd, J=8.8, 4.2 Hz, 1H, indazole), 7.34 (d, J=8.8 Hz, 2H, Ph), 7.14 (dd, J=17.6, 8.8 Hz, 1H, indazole), 6.87 (d, J=8.8 Hz, 2H, Ph), 6.02 (bs, 1H, olefinic), 3.94 (bs, Ar—CH$_2$N), 3.73 (s, 3H, OMe), 3.12 (m, 2H, C=C—CH$_2$—N), 2.68 (t, J=5.6 Hz, 2H, CH$_2$—C—N), 2.42 (bs, 2H, CH$_2$—N); MS (CI+) m/e 356 (M+H$^+$); Anal. calcd for C$_{20}$H$_{19}$N$_3$F$_2$O$_0$·H$_2$O: C, 66.47; H, 5.49; N, 11.63. Found: C, 66.35; H, 5.23; N, 11.51.

EXAMPLE 16

3-(4-Benzofuran-5-yl-3,6-dihydro-2H-pyridin-1-ylmethyl)-1H-indazole

The title compound was prepared as a white crystalline solid following the general procedure described in EXAMPLE 4; mp 193°–194° C. (from EtOAc); $^1$H NMR (360 MHz, d$_6$-DMSO) δ 12.83 (bs, 1H, NH), 7.95 (bs, 1H, benzofuran), 7.87 (d, J=7.6 Hz, 1H, indazole), 7.64 (s, 1H, benzofuran), 7.50 (m, 2H, benzofuran, indazole), 7.40–7.31 (m, 2H, benzofuran, indazole), 7.09 (t, J=7.5 Hz, 1H, indazole), 6.91 (bs, 1H, benzofuran), 6.12 (bs, 1H, olefinic), 3.96 (s, 2H, Ar—CH$_2$—N), 3.16 (bs, 2H, C=C—CH$_2$—N), 2.73 (bs, CH$_2$—C—N), 2.50 (bs, 2H, CH$_2$—N); MS (CI+) m/e 330 (M+H$^+$); Anal. calcd for C$_{21}$H$_{19}$N$_3$O: C, 76.57; H, 5.81; N, 12.76. Found: C, 76.28; H, 5.64; N, 12.59.

EXAMPLE 17

3-(4-Benzofuran-5-yl-3,6-dihydro-2H-pyridin-1-ylmethyl)-7-chloro-1H-indazole

The title compound was prepared as a white crystalline solid following the general procedure described in EXAMPLE 2; mp 218°–222° C. (from EtOAc); $^1$H NMR (360 MHz, d$_6$-DMSO) δ 13.36 (bs, 1H, NH), 7.95 (bs, 1H, benzofuran), 7.87 (d, J=7.6 Hz, 1H, indazole), 7.64 (bs, 1H, benzofuran), 7.51 (d, J=8.5 Hz, 1H, benzofuran), 7.41 (m, 2H, benzofuran, indazole), 7.11 (m, 1H, indazole), 6.91 (bs, 1H, benzofuran), 6.12 (bs, 1H, olefinic), 3.98 (s, 2H, Ar—CH$_2$N), 3.16 (bs, 2H, C=C—CH$_2$—N), 2.73 (bs, 2H, CH$_2$—C—N), 2.50 (bs, 2H, CH$_2$—N); MS (CI+) m/e (M+H$^+$); Anal. calcd for C$_{21}$H$_{18}$N$_3$OCl: C, 69.32; H, 4.99; N, 11.55. Found: C, 69.23; H, 4.78; N, 11.31.

EXAMPLE 18

3-(4-Benzo[1,3]dioxol-5-yl-3,6-dihydro-2H-pyridin-1-ylmethyl)-1H-indazole

The title compound was prepared as a white crystalline solid following the general procedure described in EXAMPLE 2; mp 139°–141° C. (from EtOAc); $^1$H NMR (360 MHz, d$_6$-DMSO) δ 12.82 (bs, 1H, NH), 7.85 (d, J=8.1 Hz, 1H, indazole), 7.48 (d, J=8.4 Hz, 1H, indazole), 7.33 (t, J=7.2 Hz, 1H, indazole), 7.08 (t, J=7.4 Hz, 1H, indazole), 7.01 (s, 1H, Ph), 6.85 (m, 2H, Ph), 6.03 (bs, 1H, olefinic), 5.98 (s, 2H, O—CH$_2$—O), 3.93 (s, 2H, Ar—CH$_2$N), 3.11 (m, 2H, C=C—CH$_2$—N), 2.68 (t, J=5.6 Hz, 2H, CH$_2$—C—N), 2.40 (bs, 2H, CH$_2$—N); MS (CI+) m/e 334.52 (M+H$^+$); Anal. calcd for C$_{20}$H$_{19}$N$_3$O$_2$o·H$_2$O: C, 71.09; H, 5.82; N, 12.44. Found: C, 71.15; H, 5.71; N, 12.22.

EXAMPLE 19

3-[4-(1H-Indol-5-yl)-3,6-dihydro-2H-pyridin-1-ylmethyl]-1H-indazole

The hydrogen oxalate salt of the title compound was prepared as a white crystalline solid following the general procedure described in EXAMPLE 2; mp 198°–200° C. (from MeOH/EtOAc); $^1$H NMR (360 MHz, d$_6$-DMSO) δ 13.35 (bs, 1H, NH), 11.10 (bs, 1H, NH), 7.97 (d, J=8.1 Hz, 1H, indazole), 7.59 (bs, 2H, indole, indazole), 7.41 (t, J=7.3 Hz, 1H, indazole), 7.33 (m, 2H, indole), 7.21 (m, 2H, indole, indazole), 6.42 (bs, 1H, indole), 6.08 (bs, 1H, olefinic), 4.58 (bs, 1H, Ar—CH$_2$—N), 3.74 (bs, 1H, Ar—CH$_2$—N), 3.32 (bs, 4H, 2×CH$_2$), 2.76 (bs, 2H, CH$_2$); MS (CI+) m/e 329 (M+H$^+$); Anal. calcd for C$_{21}$H$_{20}$N$_4$oC$_2$O$_4$H$_2$: C, 66.02; H, 5.29; N, 13.39. Found: C, 65.93; H, 5.19; N, 12.64.

EXAMPLE 20

7-Chloro-3-[4-(1H-indol-5-yl)-3,6-dihydro-2H-pyridin-1-ylmethyl]-1H-indazole

The title compound was prepared as a white crystalline solid following the general procedure described in EXAMPLE 4; mp 164°–167° C. (from EtOAc); $^1$H NMR (360 MHz, d$_6$-DMSO) δ 13.36 (bs, 1H, NH), 11.01 (bs, 1H, NH), 7.87 (d, J=8.0 Hz, 1H, indazole), 7.53 (s, 1H, indole), 7.43 (d, J=7.4 Hz, 1H, indazole), 7.30 (m, 2H, indole), 7.20 (m, 1H, indole), 7.11 (t, J=7.8 Hz, 1H, indazole), 6.38 (bs, 1H, indazole), 6.03 (bs, 1H, olefinic), 3.97 (s, 2H, Ar—CH$_2$—N), 3.15 (bs, 2H, C=C—CH$_2$—N), 2.72 (m, 2H, CH$_2$—C—N), 2.50 (bs, 2H, CH$_2$—N); MS (CI+) m/e 363 (M+H$^+$); Anal. calcd for C$_{21}$H$_{19}$N$_4$Clo·H$_2$O: C, 67.02; H, 5.49; N, 14.89. Found: C, 66.88; H, 5.16; N, 14.64.

We claim:

1. A compound of formula I, or a pharmaceutically acceptable salt or prodrug thereof:

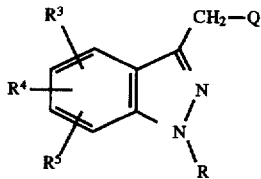

wherein

R represents hydrogen or C$_{1-6}$ alkyl;

Q represents a moiety of formula Qa, Qb or Qc:

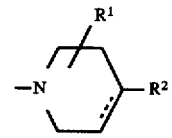

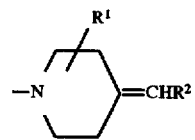

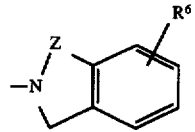

in which the broken line represents an optional chemical bond;

R$^1$ represents hydrogen, or an optionally substituted C$_{1-6}$ alkyl, C$_{1-6}$ alkoxy, C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$) alkyl, aryl(C$_{1-6}$)alkoxy, aryl(C$_{2-6}$)alkenyl, aryl(C$_{2-6}$) alkynyl, heteroaryl, heteroaryl(C$_{1-6}$)alkyl, heteroaryl (C$_{2-6}$)alkenyl or heteroaryl(C$_{2-6}$)alkynyl group;

R$^2$ represents an optionally substituted C$_{1-6}$ alkyl, C$_{1-6}$ alkoxy, C$_{2-6}$ alkenyl, C$_{2-6}$ alkynyl, C$_{3-7}$ cycloalkyl, C$_{3-7}$ cycloalkyl($C_{1-6}$)alkyl, aryl, aryl($C_{1-6}$)alkyl, aryl($C_{1-6}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^1$ or —CONR$^a$R$^b$;

Z represents —CH$_2$— or —CH$_2$CH$_2$—;

$R^6$ represents hydrogen, $C_{1-6}$ alkyl, $C_{1-6}$ alkoxy, aryl($C_{1-6}$)alkyl or halogen; and $R^a$ and $R^b$ independently represent hydrogen, hydrocarbon or a heterocyclic group.

2. A compound as claimed in claim 1 represented by formula IIA, and pharmaceutically acceptable salts and prodrugs thereof:

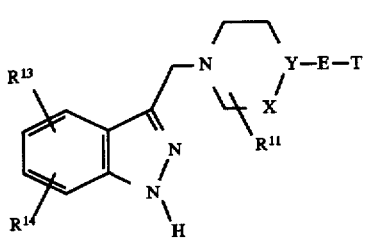
(IIA)

wherein

E represents —(CH$_2$)$_n$—, —CH=CH— or —C≡C—;

n is zero, 1, 2 or 3;

—X—Y— represents —CH$_2$—CH— or —CH=C—;

T represents a group of formula (i), (ii), (iii) or (iv):

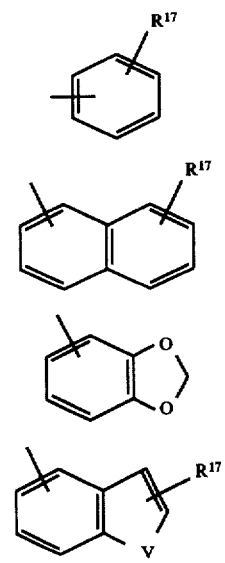

(i)

(ii)

(iii)

(iv)

in which V represents oxygen, sulphur or NH;

$R^{11}$ represents hydrogen or $C_{1-6}$ alkyl; and $R^{13}$, $R^{14}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

3. A compound as claimed in claim 2 represented by formula IIB, and pharmaceutically acceptable salts and prodrugs thereof:

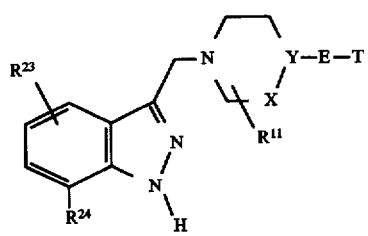
(IIB)

wherein

X, Y, $R^{11}$, E and T are as defined in claim 2; and $R^{23}$ and $R^{24}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

4. A compound as claimed in claim 2 represented by formula IIC, and pharmaceutically acceptable salts and prodrugs thereof:

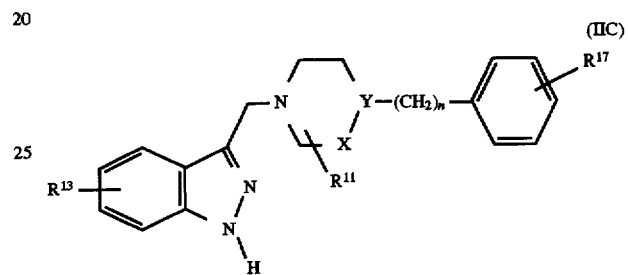
(IIC)

wherein n, X, Y, $R^{11}$, $R^{13}$ and $R^{17}$ are as defined in claim 2.

5. A compound as claimed in claim 1 represented by formula IID, and pharmaceutically acceptable salts and prodrugs thereof:

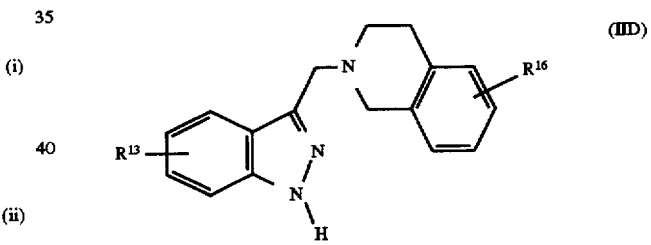
(IID)

wherein $R^{13}$ is as defined in claim 2; and $R^{16}$ represents hydrogen, $C_{1-6}$ alkyl, $C_{1-6}$ alkoxy, aryl($C_{1-6}$)alkyl or halogen.

6. A compound as claimed in claim 1 selected from:

3-(1,2,3,4-tetrahydroisoquinolin-2-ylmethyl)-1H-indazole;

3-[4-(2-phenylethyl)piperidin-1-ylmethyl]-1H-indazole;

3-[4-(2-cyclohexylethyl)piperidin-1-ylmethyl]-1H-indazole;

6-fluoro-3-(1,2,3,4-tetrahydroisoquinolin-2-ylmethyl)-1H-indazole;

7-chloro-3-(1,2,3,4-tetrahydroisoquinolin-2-ylmethyl)-1H-indazole;

6-chloro-3-(1,2,3,4-tetrahydroisoquinolin-2-ylmethyl)-1H-indazole;

7-chloro-3-[4-(2-phenylethyl)-3,6-dihydro-2H-pyridin-1-ylmethyl]-1H-indazole;

(E)-3-[4-(2-phenylethenyl)-3,6-dihydro-2H-pyridin-1-ylmethyl]-1H-indazole;

7-chloro-(E)-3-[4-(2-phenylethenyl)-3,6-dihydro-2H-pyridin-1-ylmethyl]-1H-indazole;

3-[4-(naphthalen-2-yl)-3,6-dihydro-2H-pyridin-1-ylmethyl]1H-indazole;

7-chloro-3-[4-(4-chlorophenyl)-3,6-dihydro-2H-pyridin-1-ylmethyl]-1H-indazole;

3-[4-(4-methoxyphenyl)-3,6-dihydro-2H-pyridin-1-ylmethyl]-1H-indazole;

7-chloro-3-[4-(4-methoxyphenyl)-3,6-dihydro-2H-pyridin-1-ylmethyl]-1H-indazole;

7-fluoro-3-[4-(4-methoxyphenyl)-3,6-dihydro-2H-pyridin-1-ylmethyl]-1H-indazole;

6,7-difluoro-3-[4-(4-methoxyphenyl)-3,6-dihydro-2H-pyridin-1-ylmethyl]-1H-indazole;

3-[4-(benzofuran-5-yl)-3,6-dihydro-2H-pyridin-1-ylmethyl]-1H-indazole;

3-[4-(benzofuran-5-yl)-3,6-dihydro-2H-pyridin-1-ylmethyl]-7-chloro-1H-indazole;

3-[4-(benzo[1,3]dioxolan-5-yl)-3,6-dihydro-2H-pyridin-1-ylmethyl]-1H-indazole;

3-[4-(1H-indol-5-yl)-3,6-dihydro-2H-pyridin-1-ylmethyl]-1H-indazole;

7-chloro-3-[4-(1H-indol-5-yl)-3,6-dihydro-2H-pyridin-1-ylmethyl]-1H-indazole;

and salts and prodrugs thereof.

7. A pharmaceutical composition comprising a compound as claimed in claim 1 in association with a pharmaceutically acceptable carrier.

8. A method for antagonizing the human D4 receptor, which method comprises administering to a patient in need of such treatment an effective amount of a compound as claimed in claim 1.

* * * * *